US00PP23992P2

(12) United States Plant Patent
Hartman

(10) Patent No.: US PP23,992 P2
(45) Date of Patent: Oct. 15, 2013

(54) ***CALADIUM* PLANT NAMED 'HEART'S DELIGHT'**

(50) Latin Name: *Caladium×hortulanum*
Varietal Denomination: Heart's Delight

(76) Inventor: Robert Dale Hartman, Lake Placid, FL (US)

( * ) Notice: Subject to any disclaimer, the term of this patent is extended or adjusted under 35 U.S.C. 154(b) by 130 days.

(21) Appl. No.: 13/374,463

(22) Filed: Dec. 29, 2011

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — June Hwu
(74) *Attorney, Agent, or Firm* — C. A. Whealy

(57) ABSTRACT

A new and distinct cultivar of *Caladium* plant named 'Heart's Delight', characterized by its upright and mounding plant habit; intermediate to tall plant size; uniform plant habit; vigorous and dense growth habit; lance-type leaves with red-colored venation, greyed purple-colored interveinal areas and mottled light and dark green-colored borders; and good landscape performance.

4 Drawing Sheets

Botanical designation: *Caladium×hortulanum.*
Cultivar denomination: 'HEART'S DELIGHT'.

BACKGROUND OF THE INVENTION

The present invention relates to a new and distinct cultivar of *Caladium* plant, botanically known as *Caladium×hortulanum*, commercially referred to as a lance leaf-type *Caladium* and hereinafter referred to by the name 'Heart's Delight'.

The objective of the Inventor's breeding program is to create new *Caladium* plants that have uniform plant habit, exceptional container and garden performance and attractive foliage coloration.

The new *Caladium* plant originated from a cross-pollination made by the Inventor in April, 2001 in Lake Placid, Fla. of *Caladium×hortulanum* 'White Wing', not patented, as the female, or seed, parent with *Caladium×hortulanum* 'Florida Red Ruffles', disclosed in U.S. Plant Pat. No. 13,136, as the male, or pollen, parent. The new *Caladium* plant was discovered and selected by the Inventor as a single plant within the progeny of the stated cross-pollination in a controlled outdoor nursery environment in Lake Placid, Fla. on Jun. 15, 2002.

Asexual reproduction of the new *Caladium* plant by 'chipping' the tubers (cutting the tuber into segments each segment containing an axillary bud and tuber cortical tissue) in a controlled outdoor nursery environment in Lake Placid, Fla. since Apr. 15, 2003 has shown that the unique features of this new *Caladium* plant are stable and reproduced true to type in successive generations of asexual reproduction.

SUMMARY OF THE INVENTION

Plants of the new *Caladium* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Heart's Delight'. These characteristics in combination distinguish 'Heart's Delight' as a new and distinct *Caladium* plant:

1. Upright and mounding plant habit; intermediate to tall plant size.
2. Uniform plant habit.
3. Vigorous and dense growth habit.
4. Lance-type leaves with red-colored venation, greyed purple-colored interveinal areas and mottled light and dark green-colored borders.
5. Good landscape performance and tolerant to full sun conditions.

Plants of the new *Caladium* differ primarily from plants of the female parent, 'White Wing', in the following characteristics:

1. Plants of the new *Caladium* are taller than plants of 'White Wing'.
2. Plants of the new *Caladium* and 'White Wing' differ in leaf petiole color.
3. Plants of the new *Caladium* and 'White Wing' differ in leaf coloration as leaves of plants of 'White Wing' have pink and white-colored venation and interveinal areas with mottled light and dark green-colored borders.

Plants of the new *Caladium* differ primarily from plants of the male parent, 'Florida Red Ruffles', in the following characteristics:

1. Plants of the new *Caladium* are taller and more upright than plants of 'Florida Red Ruffles'.
2. Leaves of plants of the new *Caladium* are not as undulate as leaves of plants of 'Florida Red Ruffles'.
3. Plants of the new *Caladium* and 'Florida Red Ruffles' differ in leaf coloration as leaves of plants of 'Florida Red Ruffles' have dark red-colored venation and interveinal areas and green-colored borders.

Plants of the new *Caladium* can be compared to plants of *Caladium* 'Red Frills', not patented. In side-by-side comparisons conducted in Avon Park, Fla., plants of the new *Caladium* differed primarily from plants of 'Red Frills' in the following characteristics:

1. Plants of the new *Caladium* were more upright than plants of 'Red Frills'.

2. Leaves of plants of the new *Caladium* were broader than and not as pointed as leaves of plants of 'Red Frills'.
3. Plants of the new *Caladium* and 'Red Frills' differed in leaf coloration as leaves of plants of 'Red Frills' had red-colored venation and interveinal areas and dark green-colored borders.

Plants of the new *Caladium* can also be compared to plants of *Caladium* 'Lance Whorton', not patented. In side-by-side comparisons conducted in Avon Park, Fla., plants of the new *Caladium* differed primarily from plants of 'Lance Whorton' in the following characteristics:

1. Leaves of plants of the new *Caladium* were more rounded than leaves of plants of 'Lance Whorton'.
2. Plants of the new *Caladium* and 'Lance Whorton' differed in leaf coloration as leaves of plants of 'Lance Whorton' had rose to red-colored venation with pink-colored interveinal blotches and green-colored borders.

Plants of the new *Caladium* can also be compared to plants of *Caladium* 'Rosemary', disclosed in U.S. Plant Pat. No. 20,993. In side-by-side comparisons conducted in Avon Park, Fla., plants of the new *Caladium* differed primarily from plants of 'Rosemary' in the following characteristics:

1. Plants of the new *Caladium* were more upright than plants of 'Rosemary'.
2. Plants of the new *Caladium* grew slower than plants of 'Rosemary'.
3. Plants of the new *Caladium* and 'Rosemary' differed in leaf petiole color as plants of 'Rosemary' had solid-colored leaf petioles.
4. Plants of the new *Caladium* and 'Rosemary' differed in leaf coloration as leaves of plants of 'Rosemary' had rose red-colored venation and interveinal areas and variably mottled light and dark green-colored borders.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph at the top of the first sheet is a side perspective view of a typical plant of 'Heart's Delight' grown in a 15-cm container in a shadehouse.

The photograph at the bottom of the first sheet is a comparison view of typical plants of 'Heart's Delight' grown in 15-cm containers, the plant on the right has had its tuber de-eyed and the plant on the left has not had its tuber de-eyed prior to planting.

The photograph at the top of the second sheet is a top perspective view of typical plants of 'Heart's Delight' grown in an outdoor nursery.

The photograph at the bottom of the second sheet is a close-up view of typical freshly-harvested tubers and roots of 'Heart's Delight'.

The photograph at the top of the third sheet is a comparison view of typical potted plants of the male parent, 'Florida Red Ruffles' (lower left), 'Heart's Delight' (center) and the female parent, 'White Wing' (lower right).

The photograph at the bottom of the third sheet is a close-up view of a typical inflorescence of 'Heart's Delight'.

The photograph at the top of the fourth sheet is a comparison view of typical potted plants of 'Heart's Delight' (left) and 'Red Frills' (right).

The photograph at the bottom of the fourth sheet is a side perspective view of a typical potted plant of 'Lance Whorton'.

DETAILED BOTANICAL DESCRIPTION

The aforementioned photographs and following observations and measurements describe plants grown during the spring in 15-cm containers in Avon Park, Fla. in a polypropylene-covered shadehouse (30% shade) and plants grown during the autumn in ground beds in an outdoor nursery in Zolfo Springs, Fla. All plants were grown under environmental conditions and cultural practices which approximate those generally used in commercial shadehouse and outdoor nursery *Caladium* production. During the production of the plants, day temperatures ranged from about 28° C. to 33° C. (shadehouse) or 29° C. to 35° C. (outdoor nursery), night temperatures ranged from about 22° C. to 25° C. (shadehouse) or 23° C. to 26° C. (outdoor nursery) and light levels were about 8,000 foot-candles (shadehouse) or 10,000 to 12,000 foot-candles (outdoor nursery). Plants grown in the shadehouse were seven weeks old when the photographs and the detailed description were taken. Plants grown in the outdoor nursery were six months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Heart's Delight'.

Parentage:

*Female, or seed, parent.*—*Caladium×hortulanum* 'White Wing', not patented.

*Male, or pollen, parent.*—*Caladium×hortulanum* 'Florida Red Ruffles', disclosed in U.S. Plant Pat. No. 13,136.

Propagation:

*Type.*—By "chipping" the tubers.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented; individual segments ovate to round in shape. Height: About 3.8 cm. Diameter: About 4.4 cm. Texture: Thick and starchy; somewhat brittle. Color: Epidermis, freshly harvested, close to 199A; epidermis, dried tuber, close to 200A; interior, close to 2C to 2D; axillary buds, close to 155A. Root description: Thick, fleshy contractile roots; color, close to 155A. Rooting habit: Few lateral branches; moderately dense.

Plant description:

*Plant type.*—Herbaceous perennial; suitable as a potted plant in containers 15-cm to 25-cm and suitable as a landscape plant in shaded and full sun areas.

*Plant and growth habit.*—Upright and mounding plant habit; intermediate to tall plant size; inverted triangle; vigorous and dense growth habit; rapid growth rate; petioles and leaves arise from one or more growing points on tubers; petioles mostly upright and leaning outwardly with development.

*Plant height, from soil level to top of foliar plane, shadehouse-grown potted plants*.—About 22 cm to 26 cm.

*Plant height, from soil level to top of inflorescences, shadehouse-grown potted plants*.—About 28 cm.

*Plant diameter or spread, shadehouse-grown potted plants*.—About 28 cm to 40 cm.

*Number of clumps per plant, shadehouse-grown potted plants*.—About seven from de-eyed tubers.

*Cataphylls, shadehouse-grown potted plants*.—Length: About 6 cm. Width: About 1.5 cm. Shape: Lanceolate. Apex: Acute to cuspidate. Base: Sheathing the stem. Color, outer surface: Close to 147C tinged with close to 182D and variably streaked and stippled with close to N186C and 200A; with development, color becoming closer to 200A. Color, inner surface: Close to 155C; colors visible from the outer surface.

Foliage description:

*Length, shadehouse-grown potted plants*.—About 14 cm to 23 cm.

*Width, shadehouse-grown potted plants* (*flattened*).—About 10.5 cm to 17 cm.

*Shape*.—Ovate to lanceolate.

*Apex*.—Acuminate.

*Base*.—Sagittate to cordate.

*Margin*.—Entire; broad undulations.

*Texture, upper surface*.—Smooth, glabrous.

*Texture, lower surface*.—Smooth, glabrous; glaucous.

*Venation pattern*.—Pinnate.

*Color, shadehouse-grown potted plants*.—Developing leaves, upper surface: Midrib: Close to 53A to 53B. Primary and secondary venation: Close to 53A to 53B. Interveinal areas: Close to 53B to 53C and close to 187A. Borders: Mottled light and dark green, darker than 147A and 193A to 193B and 194B. Developing leaves, lower surface: Midrib: Close to 185B to 185C. Primary venation: Close to 185B to 185C. Secondary venation: Close to 195B. Interveinal areas: Close to 185C. Borders: Between 137C and 147B. Fully expanded leaves, upper surface: Midrib: Close to 53A to 53B. Primary venation: Close to 53A to 53B. Secondary venation: Close to 187A to 187B. Interveinal areas: Close to 53B to 53C and 187A to 187A. Borders: Mottled light and dark green, darker than 147A and 193A to 193B; splotches, close to 193A to 193B. Fully expanded leaves, lower surface: Midrib: Close to 185C. Primary and secondary venation: Close to 185C. Interveinal areas: Close to 53C to 53D and close to 185C. Borders: Mottled light and dark green, close to 147B and 194A.

*Petiole*.—Aspect: Mostly erect, outwardly leaning and curving with development; flexible. Length, shadehouse-grown potted plants: About 15 cm to 19 cm. Diameter, distal, shadehouse-grown potted plants: About 3 mm. Diameter, proximal, shadehouse-grown potted plants: About 6 mm. Color, shadehouse-grown potted plants: Close to 147C, 182D or 147C tinged with close to 182D and variably streaked or boldly striped with close to N186C and 200A; below the leaf/petiole junction, close to 182B to 182C tinged with close to 147C. Wing length, shadehouse-grown potted plants: About 4.8 cm to 6 cm. Wing diameter, shadehouse-grown potted plants: About 7 mm to 8.5 mm. Wing color, shadehouse-grown potted plants, outer surface: Close to 147C tinged with close to 182D and variably streaked and stippled with close to N186C and 200A. Wing color, shadehouse-grown potted plants, inner surface: Colors visible from outer surface.

Inflorescence description: Inflorescences observed on seven-week old shadehouse-grown potted plants.

*Inflorescence arrangement*.—Upright hooded spathes surrounding a columnar spadix borne on a tall upright scape; spadix with sessile, simple female and male flowers separated into two zones; female flowers arranged on the lower one-third of the spadix; male flowers arranged on the upper two-thirds of the spadix; sterile flowers develop at junction of female and male flower zones; near this junction, the spathe constricts and surrounds and encloses the female flowers; spathe open and cupped around male flowers.

*Fragrance*.—None detected.

*Natural flowering season/longevity*: Plants of the new *Caladium* typically flower during the spring or early summer in central Florida; flowers develop about seven weeks after growth commences; inflorescences last about three days before fading; inflorescences persistent.

*Spathe*.—Length: About 12.2 cm; upper open length, about 8.4 cm and lower closed length, about 3.8 cm. Width, distal: About 3.9 cm. Width, proximal: About 2.8 cm. Width, at constriction: About 1.5 cm. Shape: Obovate. Apex: Acuminate. Base: Tapering to the peduncle. Margin: Entire; slightly reflexed. Texture, upper and lower surfaces: Smooth, glabrous. Color, front surface: Upper two-thirds: Close to 158C to 158D; with development, color becoming closer to 199A. Lower one-third: Close to 147C to 147D; towards the base, deeply colored with close to 187A; with development, color becomes closer to 147B to 147C and variably flushed with close to 184B to 184C. Color, rear surface: Upper two-thirds: Close to 145D and 146D streaked with close to 147B to 147C. Lower one-third: Close to 147B to 147C and variably flushed with close to 184B to 184C.

*Spadix*.—Length: About 8.4 cm. Length, male flower zone: About 5.2 cm. Length, sterile flower zone: About 1.2 cm. Length, female flower zone: About 2 cm. Diameter, male flower zone: About 9.5 mm. Diameter, sterile flower zone: About 6.5 mm. Diameter, female flower zone: About 1.1 cm. Shape: Columnar. Apex: Obtuse. Base: Obtuse. Aspect: Upright. Color, mature, male zone: Close to 158A to 158B. Color, mature, sterile zone: Close to 158A to 158B. Color, mature, female zone: Close to 159A and 9A. Male flowers: Quantity per spadix: About 240. Shape: Obovate. Height: About 3 mm. Diameter: About 3 mm. Pollen amount: Moderate. Pollen color: Close to 159D. Female flowers: Quantity per spadix: About 200. Shape: Obovate. Height: About 3 mm. Diameter: About 2 mm. Stigma color: Close to 159A and 9A. Ovary color: Close to 155D.

*Scape*.—Length: About 16 cm. Diameter: About 6.5 mm. Strength: Sturdy; flexible. Aspect: Erect. Texture: Smooth, glabrous; glaucous. Color: Close to 147C tinged with close to 182D and variably streaked, striped and stippled with close to N186C and 200B.

*Seeds and fruits*.—Seed and fruit development have not been observed on plants of the new *Caladium*.

Disease & pest tolerance/resistance: Plants of the new *Caladium* have been observed to have average tolerance to *Xanthomonas* Leaf Spot and *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and suitable for USDA Hardiness Zones 8A to 11.

It is claimed:

1. A new and distinct *Caladium* plant named 'Heart's Delight' as illustrated and described.

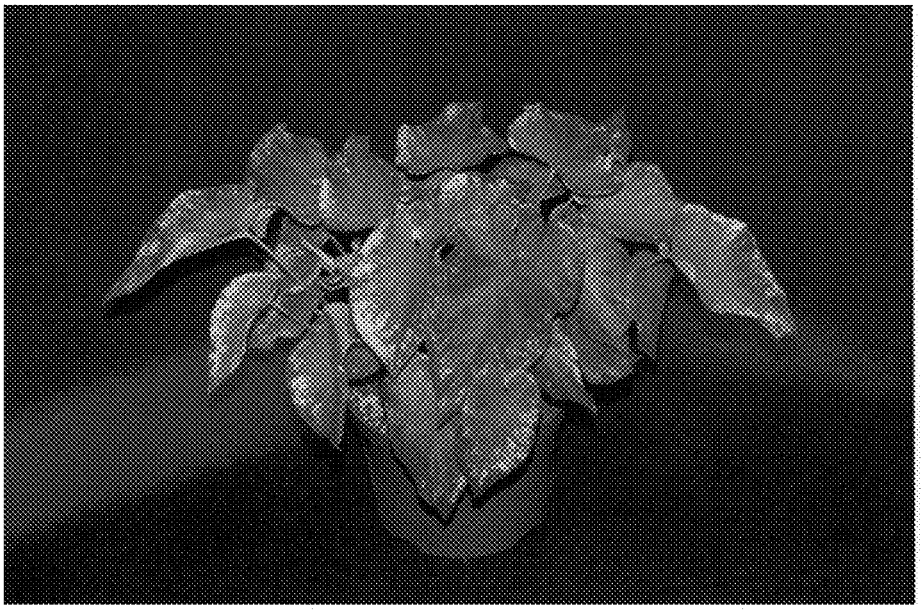
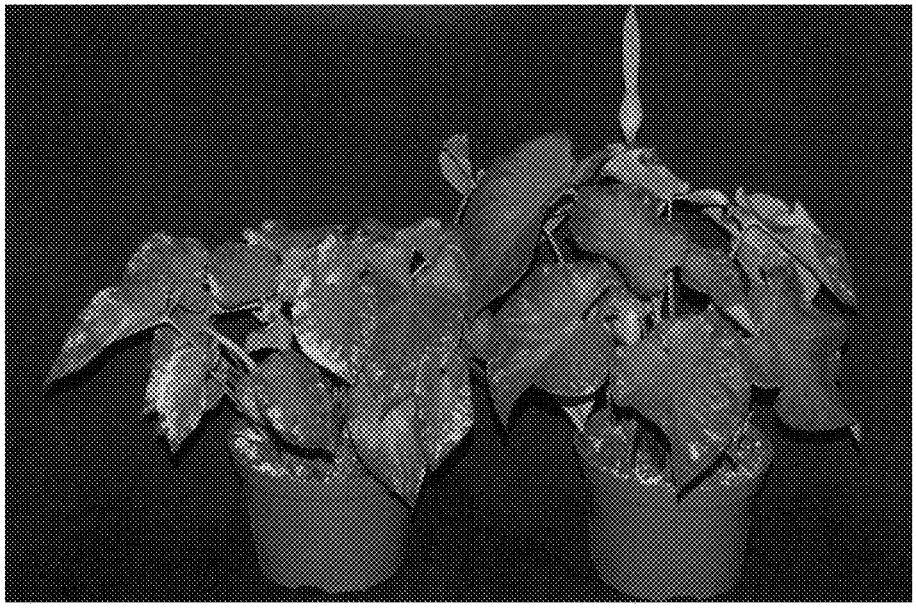

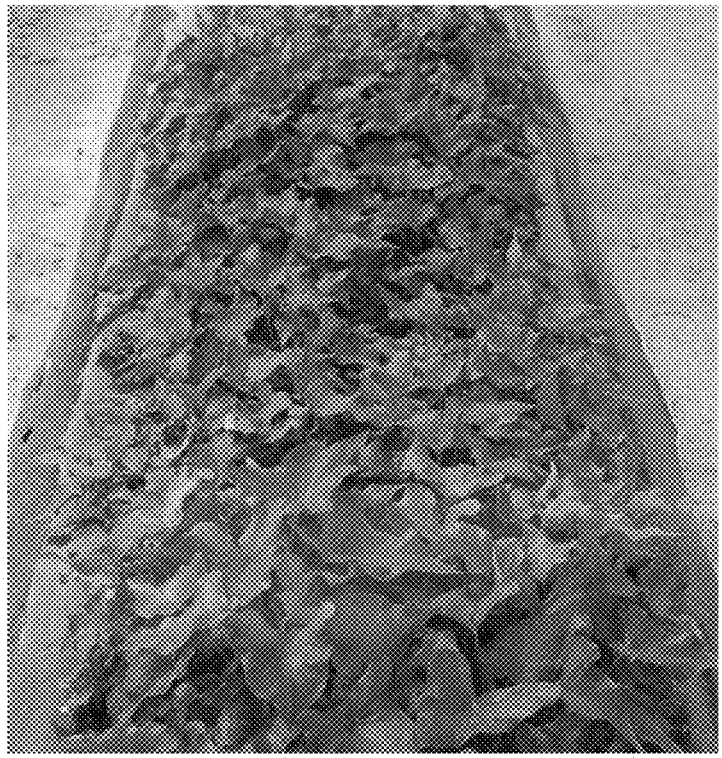
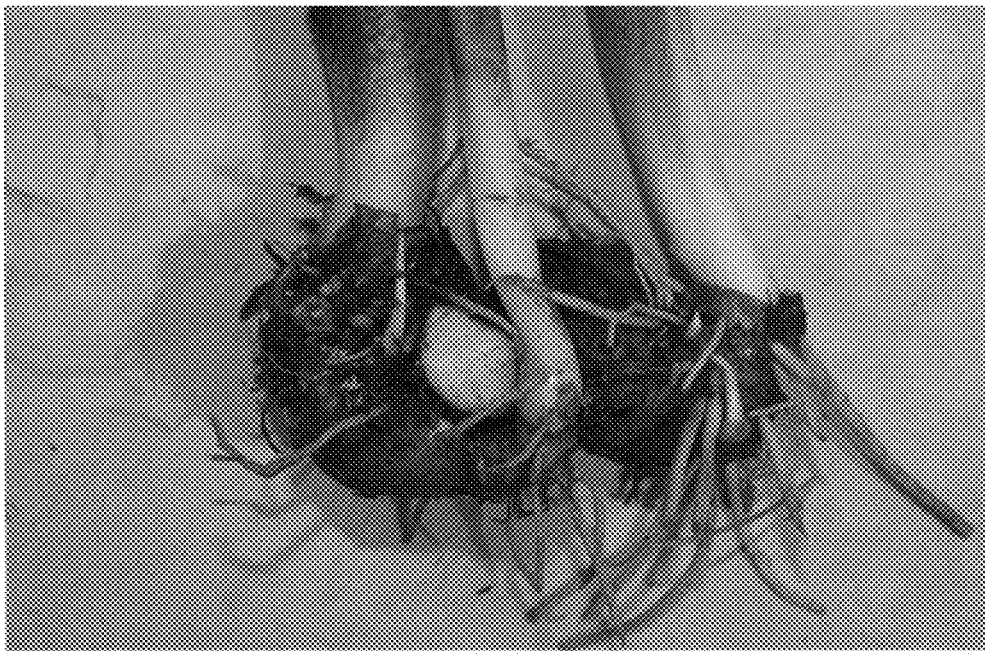

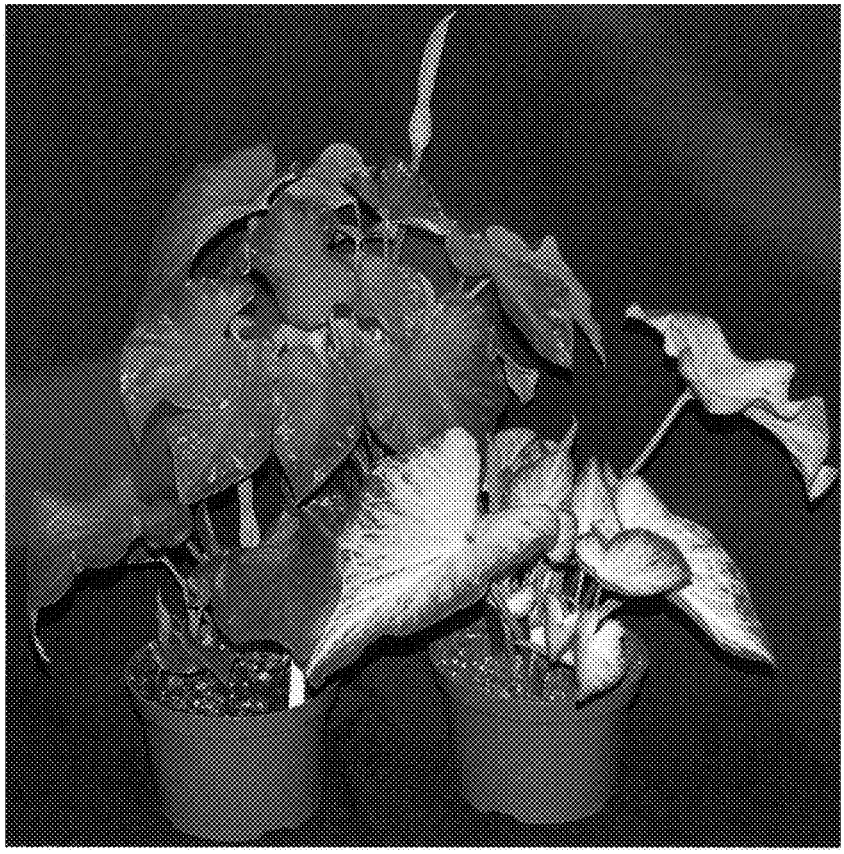
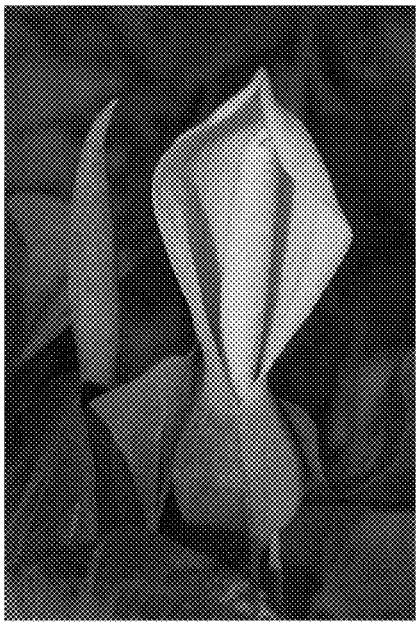

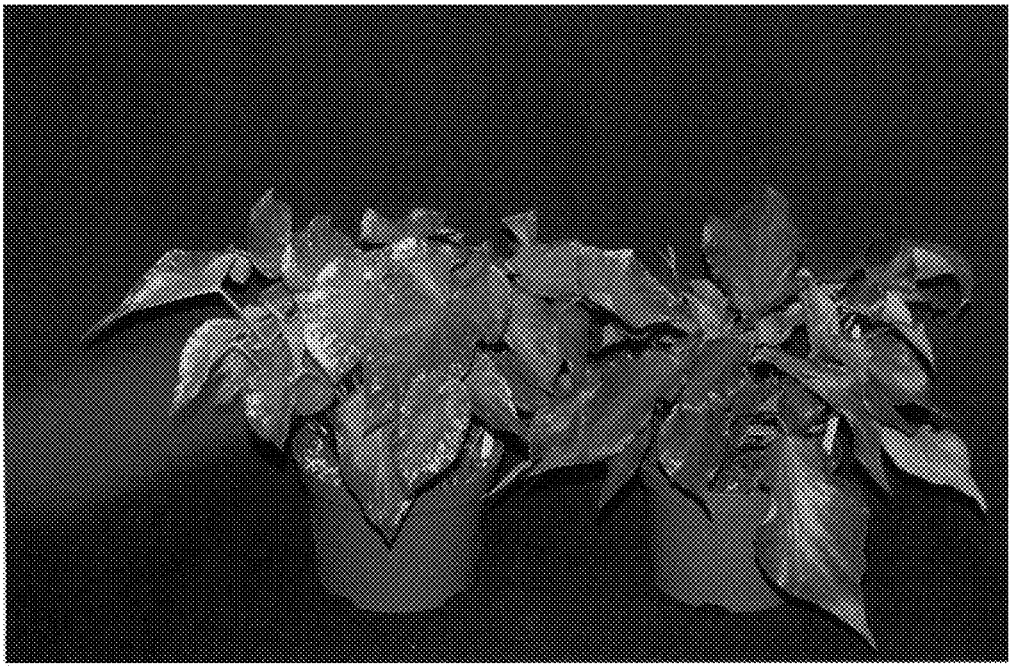
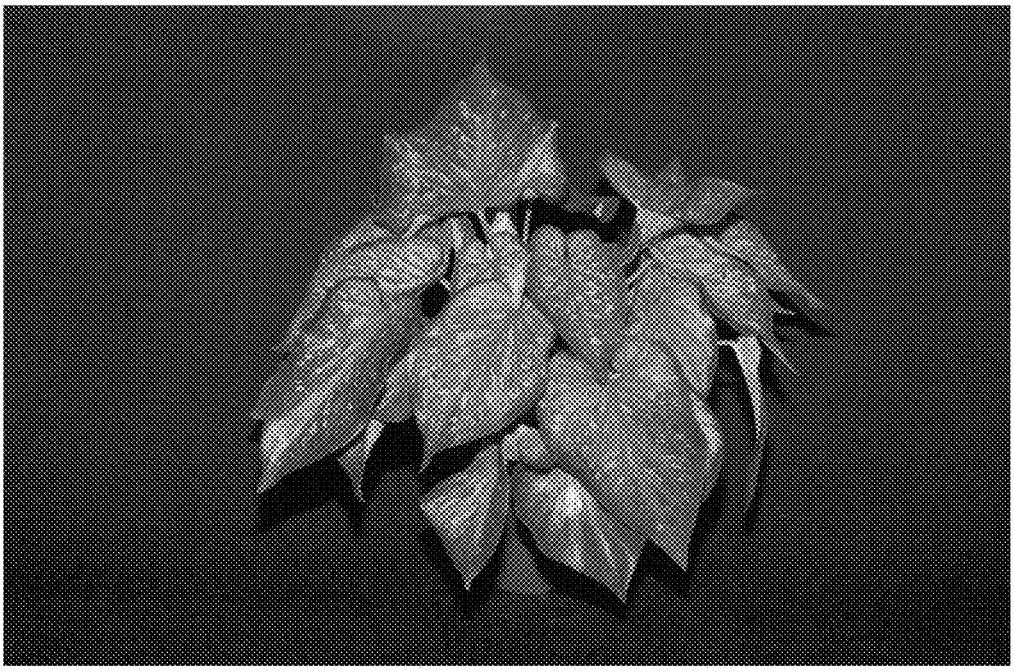

* * * * *